US 6,685,639 B1

(12) United States Patent
Wang et al.

(10) Patent No.: US 6,685,639 B1
(45) Date of Patent: Feb. 3, 2004

(54) HIGH INTENSITY FOCUSED ULTRASOUND SYSTEM FOR SCANNING AND CURING TUMOR

(75) Inventors: Zhilong Wang, Chongqing (CN); Zhibiao Wang, Chongqing (CN); Feng Wu, Chongqing (CN); Jin Bai, Chongqing (CN)

(73) Assignee: Chongqing Hifu, Chingqing (CH)

( * ) Notice: Subject to any disclaimer, the term of this patent is extended or adjusted under 35 U.S.C. 154(b) by 0 days.

(21) Appl. No.: 09/600,854

(22) PCT Filed: Dec. 18, 1998

(86) PCT No.: PCT/CN98/00310

§ 371 (c)(1),
(2), (4) Date: Sep. 11, 2000

(87) PCT Pub. No.: WO99/37364

PCT Pub. Date: Jul. 29, 1999

(30) Foreign Application Priority Data

Jan. 25, 1998 (CN) .......................... 98100283 A

(51) Int. Cl.$^7$ ................................. A61N 7/02
(52) U.S. Cl. ........................... 600/439; 601/3
(58) Field of Search ......................... 600/437, 439, 600/444, 445, 407, 473, 476; 604/22; 601/2, 3, 4; 128/915; 5/601, 600, 615; 607/96; 310/322

(56) References Cited

U.S. PATENT DOCUMENTS

| | | | | |
|---|---|---|---|---|
| 3,765,403 A | * | 10/1973 | Brenden ..................... | 600/448 |
| 4,094,306 A | * | 6/1978 | Kossoff ....................... | 73/607 |
| 4,485,819 A | * | 12/1984 | Igl ............................... | 600/445 |
| 4,646,756 A | * | 3/1987 | Watmough et al. .......... | 607/154 |
| 4,893,624 A | * | 1/1990 | Lele ............................. | 601/3 |
| 4,936,303 A | * | 6/1990 | Detwiler et al. ............. | 601/3 |
| 4,938,217 A | * | 7/1990 | Lele ............................. | 601/3 |
| 5,054,470 A | * | 10/1991 | Fry et al. ...................... | 601/2 |
| 5,247,924 A | * | 9/1993 | Suzuki et al. ................ | 600/439 |
| 5,409,002 A | * | 4/1995 | Pell .............................. | 600/407 |
| 5,501,655 A | * | 3/1996 | Rolt et al. .................... | 600/439 |
| 5,522,869 A | * | 6/1996 | Burdette et al. .............. | 601/3 |
| 5,590,653 A | * | 1/1997 | Aida et al. .................... | 600/411 |
| 5,769,790 A | * | 6/1998 | Watkins et al. .............. | 600/439 |
| 6,042,556 A | * | 3/2000 | Beach et al. .................. | 601/3 |
| 6,280,402 B1 | * | 8/2001 | Ishibashi et al. ............. | 600/439 |
| 6,425,867 B1 | * | 7/2002 | Vaezy et al. ................. | 600/439 |

* cited by examiner

*Primary Examiner*—Eleni Mantis Mercader
(74) *Attorney, Agent, or Firm*—Lowe Hauptman Gilman & Berner LLP

(57) ABSTRACT

A high intensity focused ultrasound system for scanning and treating tumor, having a combined probe, a power source, a B-mode ultrasound scanner, a multi-dimensional digit-controlled motional apparatus, a vacuum degassor apparatus, a therapeutic bed, and a computer. The combined probe comprises a B-mode ultrasound probe and a therapeutic head which generates therapeutic focused ultrasound; its ultrasound-emitting end is mounted on the multi-dimensional motional apparatus, and the motional apparatus carries out scanning movement outside the body under the control of the computer, causing the high sound intensity focal region (space-point) generated by the therapeutic head to carry out scanning within the body. By the action of high sound intensity, the temperature of the tissues in the focal region instantaneously rises to over 70 degrees centigrade and the tissues are affected by the mechanical action of cavitation, so degeneration and necrosis occur. In-this-way the tumor-within the body is treated by scanning movement outside the body.

24 Claims, 7 Drawing Sheets

HIGH INTENSITY FOCUSED ULTRASOUND SYSTEM FOR SCANNING AND CURING TUMOR

TECHNICAL FIELD

This invention relates to an ultrasonic therapeutic apparatus, particularly a high intensity focused ultrasound (HIFU) scanning and treating system for tumor, which is an apparatus utilizing the sound intensity with high energy in the HIFU focal region to scan and treat the tumor tissues.

TECHNICAL BACKGROUND

Ultrasonic wave is a mechanic energy with good directivity which can penetrate into the human body. People began to apply ultrasonic wave to the treatment and diagnosis of diseases long ago, then the ultrasonic physical therapeutic apparatuses such as A-ultrasonic apparatus, B-ultrasonic apparatus, etc. were made. The common feature of these apparatuses is that they produce very low sound intensity in the target tissue; usually the average intensity is below $3W/cm^2$. In the past 20 years, great achievements had been made in the field of ultrasonic diagnosis, and ultrasonic therapies were developed gradually and then very quickly; of which the progress in the development of ultrasonic thermotherapy and high intensity ultrasonic therapy is specially obvious.

Medical researchers have discovered that the heat-resistance of cancer cells is poorer than that of normal cells. When the temperature is between 42.5 and 45 degrees centigrade, the cancer cells die within 30 minutes while the normal cells are injured slightly and the injury is reversible. By utilizing this difference between cells and the thermal effect produced by ultrasonic wave, the ultrasonic thermo-therapeutic apparatus was produced.

By retrieval, it has been found that the patent invention CN91105010.8,—"Ultra-high speed extrinsic ultrasonic high temperature therapeutic apparatus"—belongs to the kind of apparatus mentioned above; the outstanding point of this patent invention is that treatments with sound intensity for a certain point (e.g. the center) of the target is carried out repeatedly; then the cells and tissues of the target (the tumor) are damaged by the diffusion of heat produced at the point. However, the effect of the apparatus is poor; the following are the reasons: 1. the active cancer cells are distributed mainly on the margin of the cancer mass; but the increase of temperature on the margin is relatively low; 2. The mass of cancer itself is irregular in shape, the shape of heat diffusion is difficult to control and there is temperature gradient; the non-invasive temperature measuring technique for tissues in deep parts of the body, especially the measurement of temperature increase and temperature gradient within the heat diffusion volume, is a worldwide difficult problem; 3. in order to put the irregular cancer mass under complete irradiation, it is unavoidable that the large amount of normal tissues are injured; 4. B-type echo detector is used within very short intervals between therapeutic wave beams to catch echo and to examine the A-type echo image of the degree of target damage during treatment; for this purpose, special image-storing circuit and sampling-comparing circuit are used; because only two successive A-type ultrasonic images are stored, it is difficult to observe the therapeutic effects directly; also it will make the apparatus complicated. 5. The therapeutic head can not aim at the target to carry out scanning movement, so the range of treatment is limited; it can not be used to treat the diffused point-like, branched, stripe-shaped, or other irregular shaped targets, or targets in relatively special locations.

Another patent application, CN93100813.1 shows "A Method and an Apparatus which aims at the Target of Human Tissues to Carry out Treatment". It puts stress on the description of a method aiming at the target of human tissues; in the method, a real-time acoustic distance-measuring recording probe and a therapeutic wave beam generator probe are used, and a visible reference mark is used to determine the theoretical location of one reference point in two wave beams; by means of the relative focus F in the coordinate system and the reference mark R the predetermined displacement is made, and by causing the visible reference marks of the acoustic distance-measuring record image to coincide and then displacing the mentioned therapeutic generator until the mentioned first and second reference marks coincide, one focus F of the therapeutic wave beam and the mentioned target are made to coincide. The apparatus can be used to give localized treatment for prostate only and its application to other parts of human body shows no significance.

A Europeans patent number EP0734742A2 shows the characteristics of an ultrasonic therapeutic equipment: By the action of first grade base frequency, the therapeutic ultrasound generator has the property of resonance oscillation. The driver drives the therapeutic ultrasound generator to work with the driving signal of the first grade base frequency. Using the driving signal of the second grade base frequency, the driver drives the ultrasonic probe to get ultrasonic image within the body, and receive the reflected wave of the first grade ultrasonic wave produced by the therapeutic ultrasound generator as well as the reflected wave of the second ultrasonic wave generated by the ultrasonic probe. The inventor has made effort to make a perfect combination of therapeutic ultrasound and image-displaying ultrasound, in the document, 14 modes are listed.

In recent years, in order to avoid the disadvantages of thermotherapy, people have made a lot of researches on the treatment of cancer with high intensity focused ultrasound (HIFU); in the so called HIFU therapy, the ultrasound emitted by the probe with relatively low average sound intensity (usually several $W/M^2$) is focused or made to converge on a point of space, then a focal region with an average sound intensity over $1000W/M^2$ is formed; in the region instantaneous temperature elevation (>70 degrees centigrade) occurs, and cavitation or mechanical vibration occur, so the tissues in the focal region are damaged and the disease is cured.

A malignant tumor tissue has three marked characteristics: 1. because it is a tissue made up of juvenile cells, it is more sensitive to ultrasonic wave than the normal tissues. 2. it exists within the human body in three forms: a. in diffused point-like distribution, b. in the shape of a big mass, c. in the shape of tree-branches; 3. the malignancy degree of the tumor cells on the margin of the tumor is higher than that in the core of the tumor.

When the treatment of tumor tissue is carried out, injury of the normal tissue should be reduced as far as possible. The following are the difficulties in using HIFU technique to treat tumors: 1. a high energy point of ultrasonic wave (focal region) must be formed, and the ratio between the long axis and short axis of the focus region must be small; 2. the target tissue to be treated should be visible so that the location and shape of the tumor can be determined easily; 3. it should be possible to carry out scanning therapy for irregular tumors, and there should be various scanning forms for medical workers to choose. 4. it should be possible to perform real-time monitoring on the therapeutic effects. If B-mode ultrasound scanner is used for monitoring, strong ultrasonic reflection interfering B-ultrasonic image should be avoided, 5. the medium used should be a special liquid; the characteristic of its acoustic impedance should be similar to that of human tissues, and its acoustic attenuation should be little so that it will not interfere with the focused sound field.

GENERAL DESCRIPTION OF THE INVENTION

According to the technical difficulties found in the treatment for tumors with HIFU, the purpose of developing this invention is to provide a high intensity focused ultrasonic system for scanning and treating tumors. By means of focusing, the system causes ultrasonic waves to form a space-point with high energy (focal region); the energy of the region reaches over $1000W/M^2$ and the temperature instantaneously rises to >70 degrees centigrade; besides, the focal region is made to enter the tumor tissue within the human body to carry out scanning movement, guaranteeing that its locus fully covers the tumor tissues to treat the tumor.

In order to realize the above purpose, the following design is adopted in the invention: the high intensity focused ultrasonic system for scanning and treating tumor comprises a combined probe, a high intensity power source, a B-mode ultrasound scanner, a multi-dimensional digit-controlled motional apparatus, a vacuum degassor, a therapeutic bed, and a computer operation system, of which, the combined probe comprises a therapeutic head which generates therapeutic ultrasonic waves and a image-displaying probe of B-mode ultrasound scanner; it is mounted on a motional apparatus which is made up of three-dimensional rectangular coordinate and one or two dimensional rotational coordinate. The upper end of the combined probe is connected to the central hole of the therapeutic bed through an open water bag; at the middle of the therapeutic bed there is a big hole for mounting the water bag (2); the lower end of the water bag (2) is connected to the head of the combined probe (3); the combined probe (3) is mounted on the motional system (4) with three-dimensional rectangular coordinate and two dimensional rotational coordinate; the combined probe (3) is also connected to the high frequency electric power source (6); the B-mode ultrasound probe is mounted on the central axis of the combined probe and connected to the B-mode ultrasound scanner: the motional system (4) is connected to the digit-controlled scanning system; the water bag (2) is connected to the vacuum degassor (5); the computer operation system (9) is separately connected to the high frequency electric power source (6), B-mode ultrasound scanner (7), digit-controlled scanning system (8), and the vacuum degassor.

SUMMARY OF THE INVENTION

The B-mode ultrasound probe is mounted on the central part of the therapeutic head; through adjustment, it is guaranteed that the space-point (focal region) produced by the therapeutic probe falls within the image-displaying plane of B-mode ultrasound scanner. The ultrasonic wave-emitting surface of the combined probe is located under the part to be treated and it is coupled to the skin by means of the open water bag; the medium used for this coupling is a kind of vacuum degassed water whose acoustic impedance is similar to that of human body and whose acoustic attenuation is little.

By means of the ball-screw, the stepping electric motor of the motional apparatus mentioned above drives the tract base to move on the ball tract. The real location of the movement is controlled by the location sensor which takes the location signal to realize the closed-loop control of the motional system; the multi-dimensional motional apparatus is formed by the combination and repeat addition of a certain number of single dimensional motional apparatuses.

The high frequency power source mentioned above comprises a signal source, a signal modulator, a magnifier, a matching box, a three-phase electric supply, a manual controller, an interface of computer, and a display device. The signal modulator is connected separately to the three-phase electric supply, signal source, interface of the computer, and the magnifier; the signal source is connected separately to the three-dimensional electric supply, magnifier, display device, manual controller; the magnifier is connected respectively to the three-phase electric supply and the matching box; the matching apparatus gives out 0.2–0.3 MHz high frequency continuous or pulse electric supply; the signal source gives out high frequency sine wave signal of low pressure small current, which is adjusted by the signal modulation electric circuit into continuous or 10–1000 Hz carrier wave signal. The vacuum degassor mentioned above is a vacuum degasification circulating water apparatus, which comprises a vacuum pump, a circulating water pump, a water box, a regulator of water temperature, a water bag of combined probe, and a controlling electric circuit. The water box is connected separately to the vacuum pump, regulator of water temperature, circulating water pump and the water bag of the combined probe; the controlling electric circuit is connected separately to the circulating water pump, regulator of water temperature, and the vacuum pump; the combined probe and water bag are connected separately to the circulating water pump. This apparatus conducts degasification on water, then the water is used as the medium for ultrasonic coupling.

Under the control of information-processing system, the multi-dimensional digit-controlled scanning system drives the stepping motor and puts the combined probe in motion to carry out two or three dimensional scanning movement, so that two or three dimensional scanning treatment or detect is performed on the target tissue within the body by the focal region (space-point) of the combined probe.

following are the advantages of the above therapy: 1. No surgery needed, little pain suffering; 2. the tumor scanned and ablated by HIFU remains within the body; medical researches show that when the treated tumor tissue is left in the body it can strengthen the immunity of the body; and can eventually be absorbed by the body and fibrosis occurs.

When the system mentioned-above is used, the tumor tissue is searched for by the sector scanning plane of the B-ultrasonic detector and the range to be treated is determined by the medical worker. The focal region of the therapeutic head is set at a location on the sector scanning plane of the B-mode ultrasound scanner through mounting, and the position is stored in computer memory. The computer, controlled by the medical worker, gives instructions to the digit-controlled scanning system and drives the therapeutic head to carry out the scanning movement; at the same time it gives instructions to the power source to turn on or off and adjust the strength of its power. Because the location of the focal region is in a fixed relation with the therapeutic head, and its movement parallels with that of local region, so the scanning movement of the therapeutic head outside the body guarantees that the focal region carries out scanning movement within the body.

DESCRIPTION OF THE DRAWINGS

In order to make certain that the above-said design can be carried out the following procedures arc adopted: the design is further explained by figures.

Figures and simple explanations

The following are the figures for the description of the invention

Figure 1:
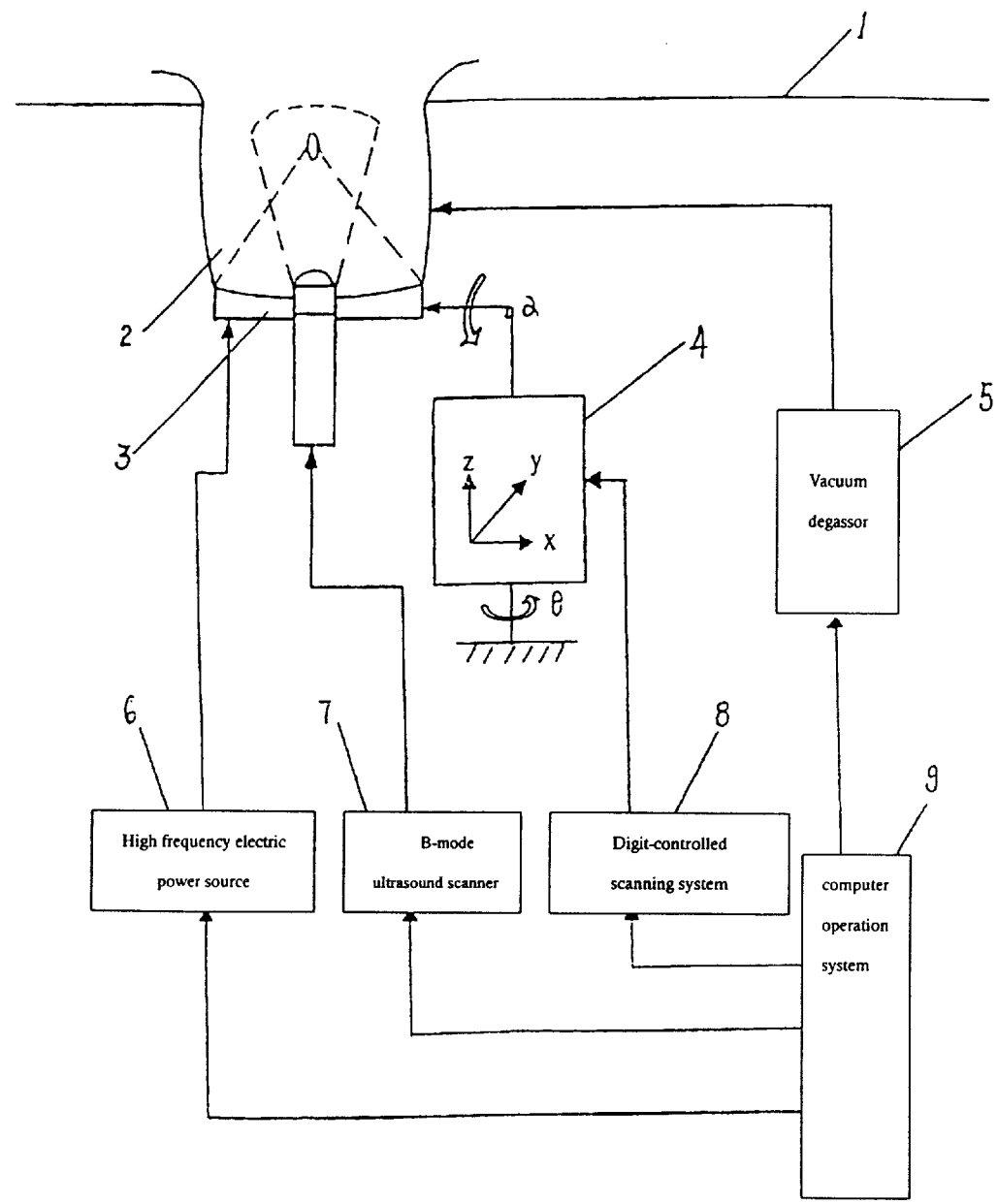

FIG. 1. Figure to illustrate the structure of the invention

Figure 2:
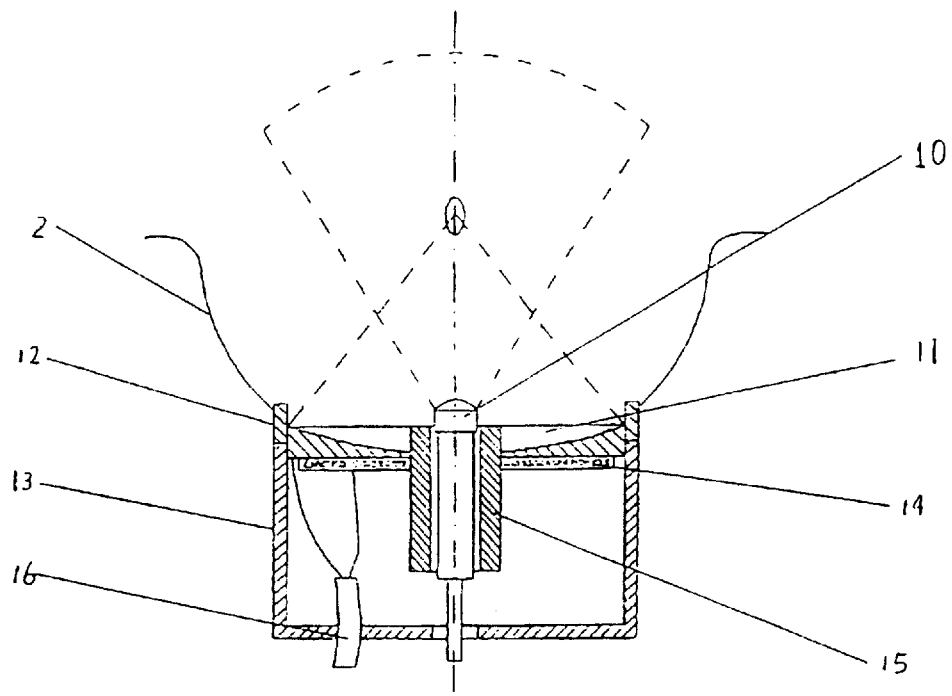
Figure 3:
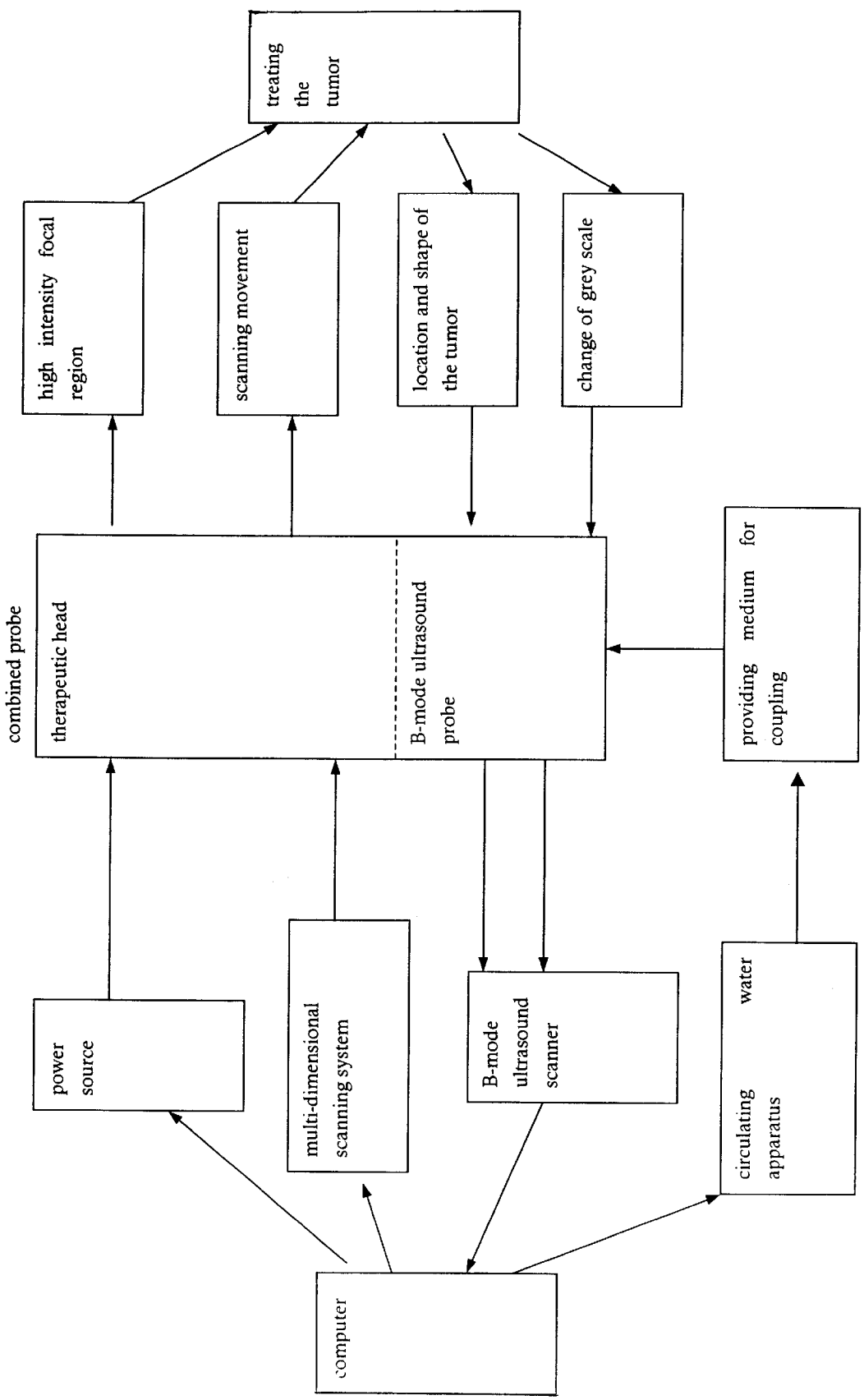

FIG. 2. Figure to illustrate the structure of the combined probe of the invention FIG. 3. Figure to illustrate the functions of the invention FIG. 4. Figure to illustrate the ultrasonic high frequency electric supply FIG. 5. Figure to illustrate the vacuum degassor FIG. 6a, FIG. 6b Flow-process diagrams of the computer operating system The Embodiments

DETAILED DESCRIPTION OF THE INVENTION

The structure of the combined probe is shown by FIG. 2. The image-displaying probe of the B-mode ultrasound scanner (1) is mounted on the axis of the therapeutic head to guarantee that the focal region (space-point) falls on the B-ultrasonic scanning plane. Because the sound intensity in the focal region produced by the therapeutic head is 100W/cm$^2$ to 10000W/cm$^2$ or more, the temperature of the tumor tissue in the focal region is very high (>70 degrees centigrade); the high temperature leads to degeneration and necrosis of the tissues and further increases the high sound impedance there; so strong echo light beam is produced in the B-ultrasonic image. In this way the special location of the therapeutic point can be monitored and the effective degree of the therapy can be reflected objectively by the change of grey scale.

Piezoelectric ceramics (14) is mounted at the back end of the therapeutic head; the electric supply driving the piezoelectric ceramic to produce ultrasonic wave is provided by the cable (16). The whole combined probe is mounted within a shielded shell (13); The water bag base (12) and water bag (2) are mounted at the front end of the shielded shell; on the core of probe (15) there is an ultrasonic wave lens (11) and at the center of the probe core is the B-mode ultrasound probe.

The combined probe mentioned-above is assembled from the lower parts upwards; this assembling method can reduce the movement of body position caused by respiration because therapy is carried out under the body when the patient is in prone position; besides, the skin of human body is in direct contact with the degassed water, so the reflex injury produced when the high intensity ultrasound goes through the skin surface can be reduced. By experiments, on animals, it has been proved that this assembling method is a practical design.

The technical parameters of the combined detector:

1. Focal distance: 40–280 mm
2. The working frequency of the therapeutic ultrasound: 0.2–3.5 MHz
3. The shape of the focal region: ellipsoid-shaped short diameter: 1.1–5 mm long diameter: 3.5–12 mm
4. The highest sound intensity at the center of the focal region: over 1000W/cm$^2$
5. Focusing angle: 30–120 degrees The functions of HIFU system for treating tumor are showed in FIG. 3.

The power source gives out high frequency electric supply, causing the therapeutic head to emit high intensity focused ultrasound and form a high intensity focal region, so that the tumor there is damaged. The multi-dimensional scanning system drives the combined probe to carry out scanning movement, causing the focal region to produce scanning locus to damage the tumor. During the process of therapy, the location and shape of the tumor and the change of therapeutic grey scale are all monitored by the B-mode ultrasound probe of the combined detector and observed by means of the screen of the B-mode ultrasound scanner. The whole process of the therapy is under to control of the computer program designed by medical workers and monitored by the computer. The scanning movement of the combined detector causes water level to change and the therapeutic head needs cooling, so the computer also automatically controls the circulating water apparatus.

The key to realize the above system lies in the combined probe. Using this probe the damage within tissue can be caused by striking the skin over the points.

Figure 4:
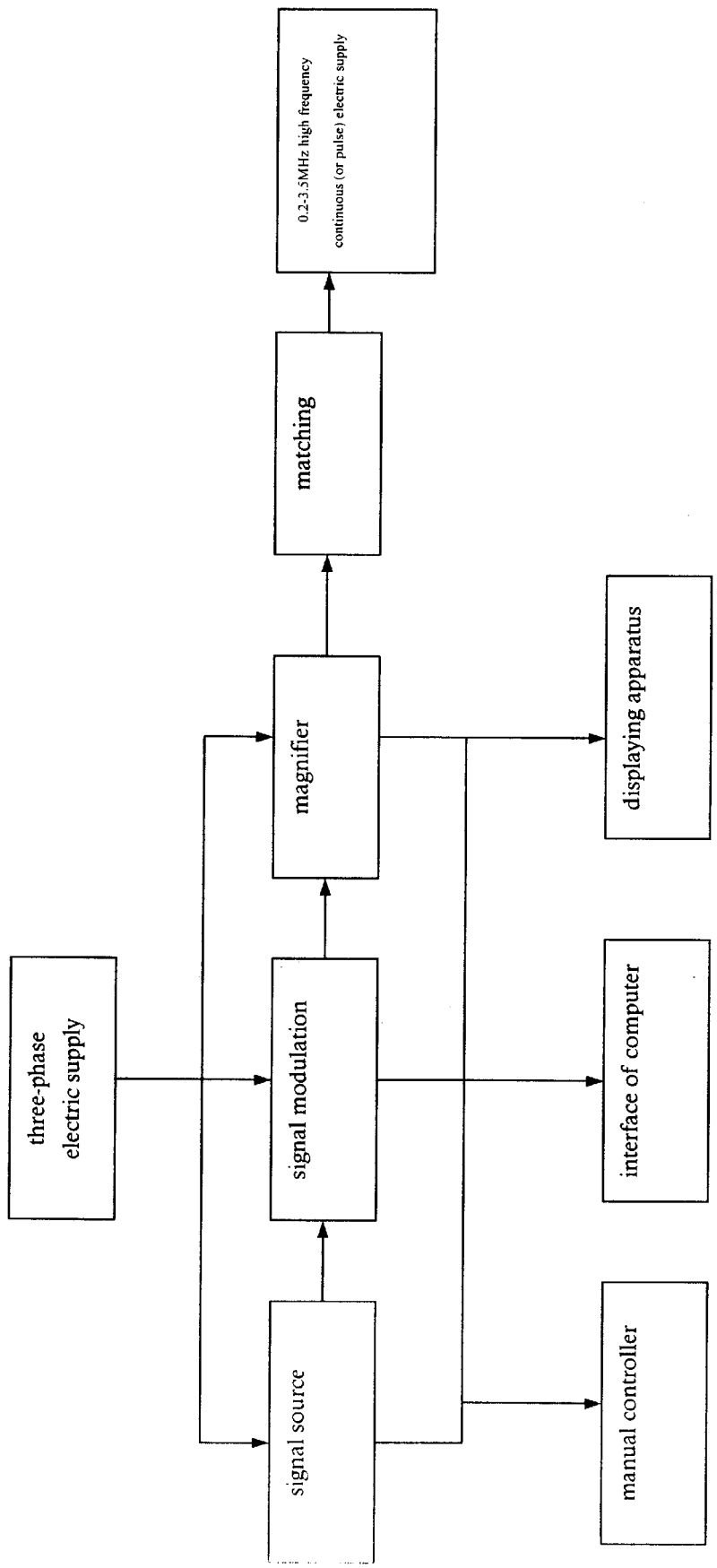

The power generator is the apparatus providing therapeutic ultrasonic high frequency electric supply, the principle of which is shown by FIG. 4. In this power source, the signal source provides low pressure 0.2–3.5 MHz high frequency sine wave signal, which is then modulated by signal modulator into low frequency carrier signal of 10–1000 Hz or continuous wave; the modulated signal is sent to the magnifier to be duplicated, magnified and sent out. Because there is relatively great difference between the impedance of the therapeutic head and that of the power source, and different probes have different kinds of impedance, so a matching circuit is added to the location between the magnifier and the probe to guarantee the best matching between them.

The B-mode ultrasound scanner provides image-displaying and monitoring functions of the combined probe. The apparatus used is the ready-made apparatus available in the market; Its main functions are the same as those B-mode ultrasound scanner used commonly. Hence, there is no need for further description.

In the motional system, the ball-screw is driven by the stepping electric motor to move on the ball tract; this mode is highly accurate with little noise, and raster distance-measurement closed-loop control is used, so the influence of step-failing out produced by the stepping electric motor can be reduced.

Figure 5:
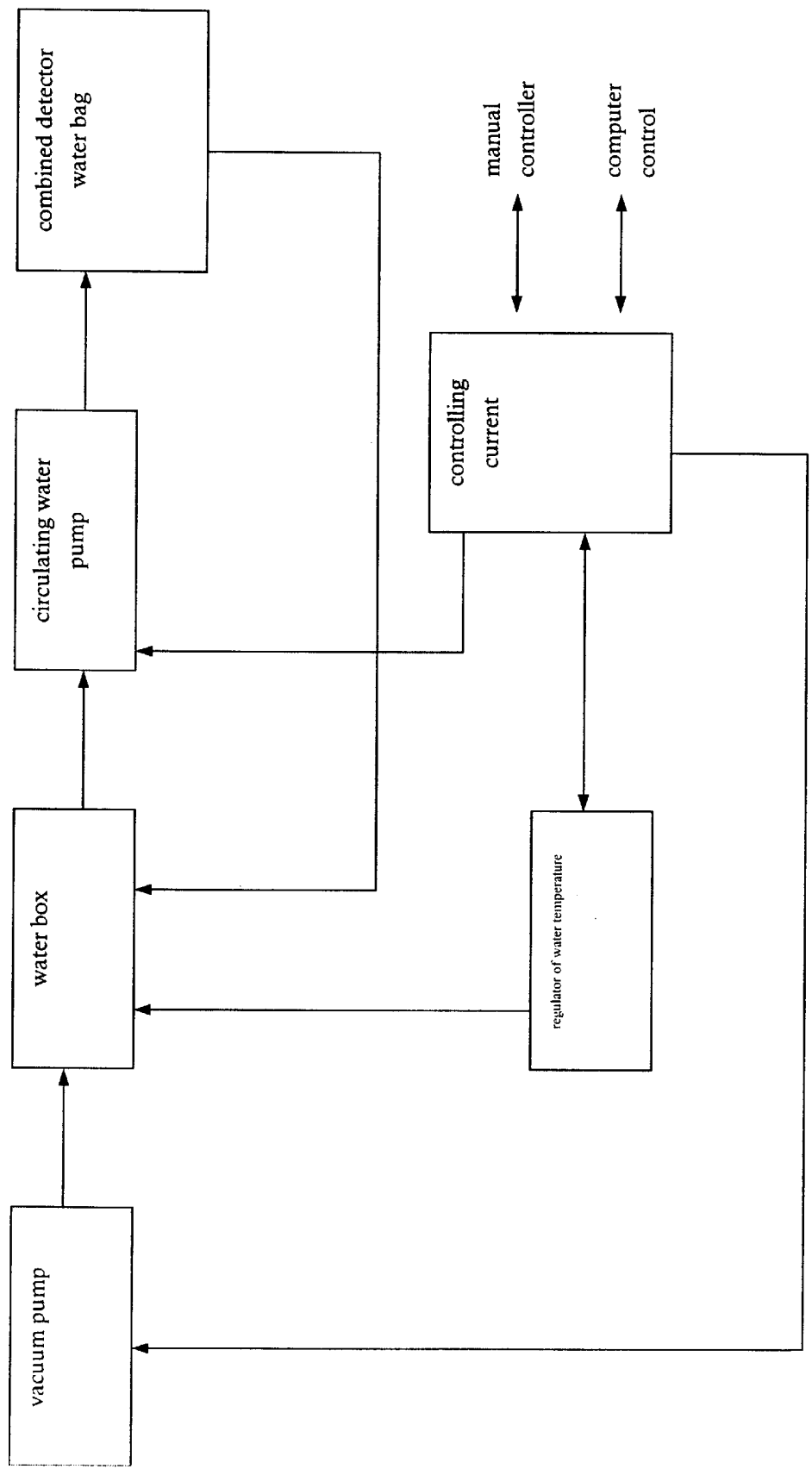
Figure 6A:
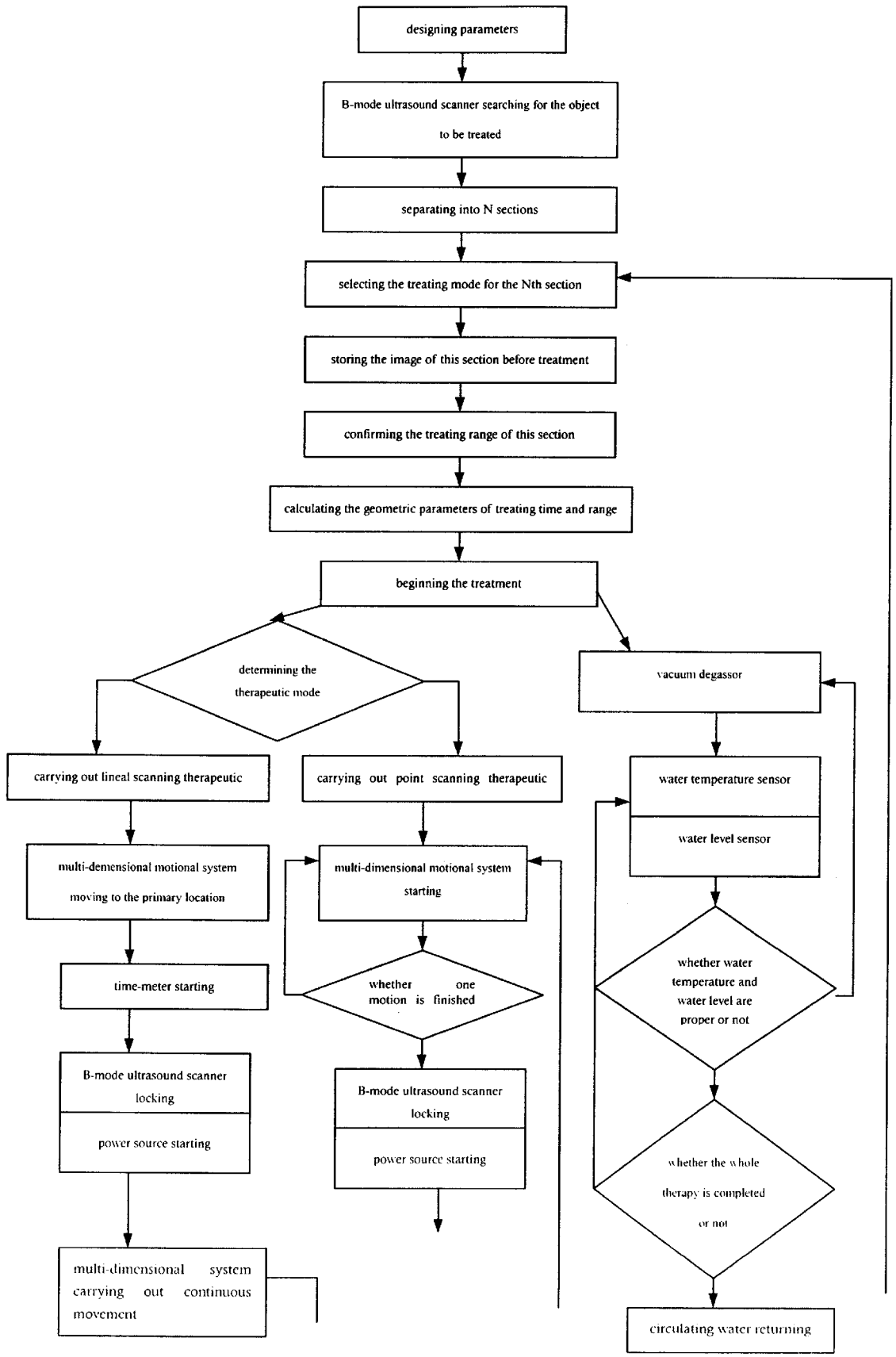
Figure 6B:
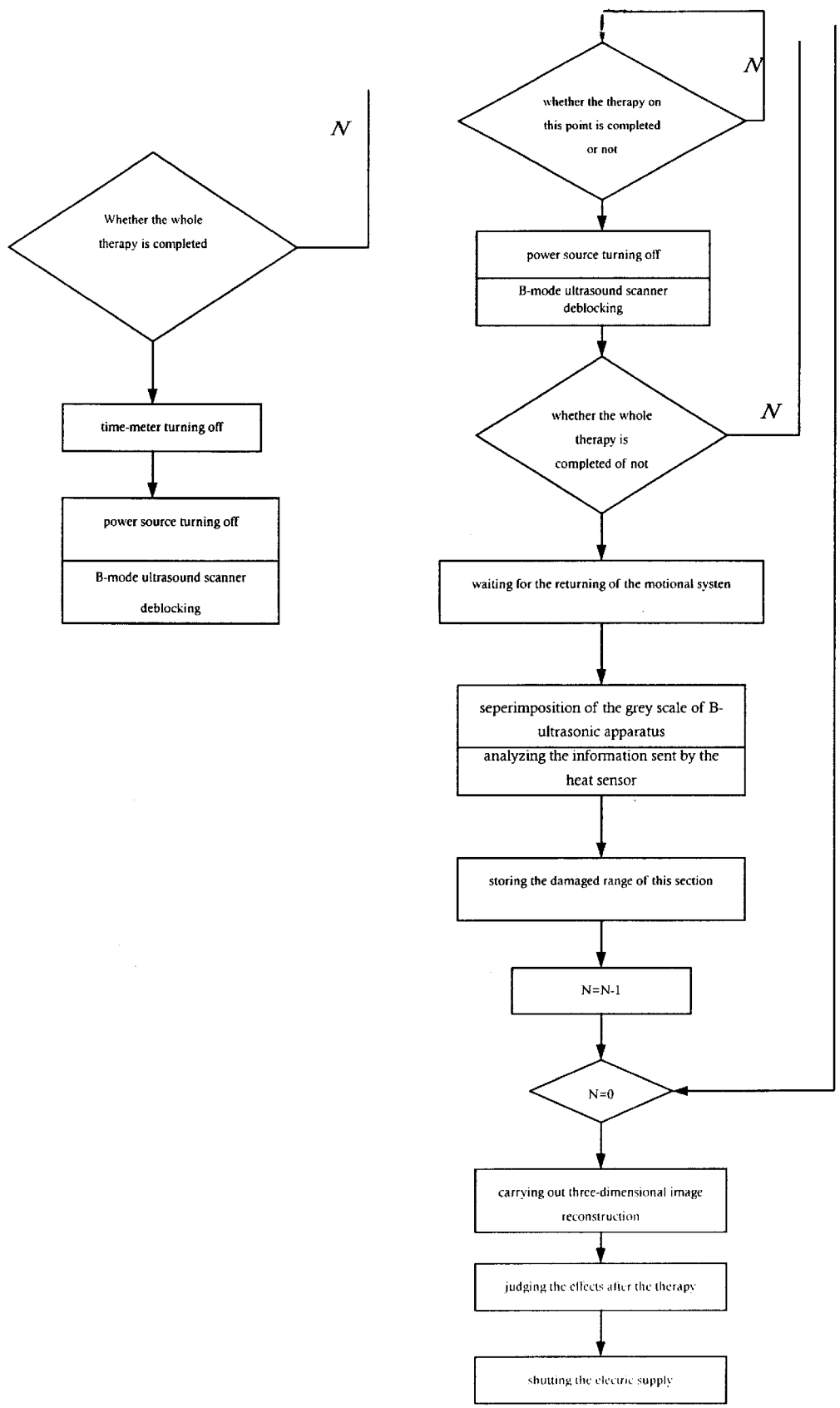

The vacuum degassor comprises a vacuum degassing water box, a vacuum pump, a circulating water pump, a regulator of water temperature, and a controlling part, which are shown by FIG. 5.

The following are shown by FIG. 6:

The main functions of image-processing and digit-controlled system of the computer are:

1. The B-mode ultrasound scanner carries out topographic scanning of tissues, then three-dimensional reconstruction processing is carried out through the computer.
2. The treatment plan and parameters are chosen by the medical workers according to the shape of the tumor.
3. The scanning system is controlled and scanning therapy carried out according to the therapeutic margin determined by the medical workers.
4. According to the difference between the grey scale of the target point before and after the treatment, grey scale operation is carried out, then the therapeutic effects are judged.
5. The intensity of ultrasonic irradiation is adjusted and energy is supplemented according to the change in therapeutic depth.

The following are the therapeutic modes of HIFU system for scanning and treating tumor:

1. Fixed-point damaging therapy: it is shown by FIG. 6; this mode is mainly used to treat tumor tissue less than 1 cm³ and diffused small tumor masses.

The characteristic of this mode: the location of the target tissue is found by the motional apparatus, then the therapy is carried out without movement. Within a B-ultrasonic topographic plane, one or more points can be treated separately.

2. Combined successive points damaging therapy: this mode is mainly used to treat the whole mass of a tumor tissue larger than 1 cm³.

The characteristic of this mode: After the location of the target tissue is detected by the motional apparatus, the therapy is carried out through discontinuous movement. A damaged mass is formed by single damaged points; $1/10-1/2$ of two damaged points coincide to guarantee that the tumor tissue treated is fully covered by the therapy; besides, there is proper overlapping on each tomographic scanning plane, which guarantees the whole mass of the tumor can be fully damaged.

3. Continuous damaging therapy: irradiation lasting for a relatively long time (e.g. 30s) is used only once; during the irradiation process, the coordinate system carries out two or three dimensional movement, causing the focal region to carry out continuous "ablation" within the body. This mode is especially suitable for the treatment of tumor tissue which is long stripe-shaped.

The characteristic of this mode: after the location of the target tissue is detected by the motional apparatus, the therapy is carried out through continuous movement. The total irradiation time and speed of movement are fixed, and different points of the tumor tissue all receive the same amount of ultrasonic irradiation.

4. A therapy combining all the above three modes can he used.

The following methods are used to guarantee that the above patent design is put into use:

1. Apply the highest ratio of energy comparision (the ratio between the average sound intensity in the focal region and that on the surface of the probe) when possible, which is shown by FIG. 1. The selection of frequency parameter and the technique of making the probe are the keys to the increase of the ratio between energy changes, regardless of the acoustic attenuation, $Ia=(D/d)^2 ID$.

2. When the ratio between energy changes is guaranteed, use the least acoustic attenuation process. Recently it has been known that the least acoustic attenuation coefficient is that of the vacuum degassed water. According to the authors' research, it is the most practical design to use vacuum degassed water as the coupling medium; frequencies of 0.2–3.5 MHz can be used according to different requirements of the therapy.

3. Use B-mode ultrasound scanner as the image-displaying apparatus. The technique of B-mode ultrasound scanner is mature, so its probe can be mounted easily on the core of the therapeutic head, and the focal region of the therapeutic head can be easily mounted within the B-ultrasonic sector scanning plane, which are shown by FIG. 2. Experiment has showed that by using this mode the location of the focal region of the therapeutic head on the sector scanning plane can be easily determined, and the computer can be made to memorize this location, then scanning movement can be carried out.

4. Use four-coordinate digit-controlled scanning and one-coordinate rotational apparatus; the reasons for this are: tumor tissue is three-dimensional tissue, in order to treat it completely with scanning therapy, it is necessary to use at least three-dimensional coordinate movement. To treat some tissues in the human body such as liver tissue, only three-dimensional rectangular coordinate scanning is needed; to treat some other tissues of the body such as the mammary tissue, the best method is using two-dimensional rectangular coordinate and one-dimensional rotational coordinate to carry out scanning. Besides, usually the mammary tumor develops on the base of the mamma, so the best thing to do is to use a manual rotational coordinate to tilt the combined probe during the treatment, usually the probe is made to include at an angle of 0–60 degrees to the perpendicular direction.

5. The whole process of scanning therapy should be controlled by the computer automatically, the reasons for this are: (1) irregular scanning routes must be used for the tumor tissue is irregular; (2) During the treatment, the therapeutic depth changes; in order to guarantee that all the tumor tissues at different distances from the surface receive the same dosage of ultrasonic irradiation, energy should be supplemented automatically according to the change in depth. (3) Because the difference between the grey scale on the ultrasonic screen before and after treatment is great, the grey scale operations before and after treatment will show the objective therapeutic effects. (4) It is also important to carry out self-monitoring of the therapy.

6. In order to prevent the interference in the B-ultrasonic image by HIFU, discontinuous working method is used. Controlled by the computer, the power source, B-mode ultrasound scanner, and the digit-controlled apparatus all work discontinuously. After early-stage sampling of the B-ultrasound scanner, the computer memorizes the image and gives instructions to the digit-controlled apparatus to carry out movement; when the next location is reached, the computer memorizes the late-stage sampling image of the B-ultrasonic apparatus and gives instructions to the power source to turn on the machine, initiating its work; then a cycle is completed. Using the early-stage sampling image of the second cycle and the late-stage sampling image of the first cycle, the computer performs grey scale calculation; by doing so the therapeutic effects can be judged according to the change in grey scale.

The sector scanning plane of the B-mode ultrasound probe is used to search for the tumor tissue, and the therapeutic range is determined by the medical worker. The location of the focal region of the therapeutic probe is set in a position within the B-ultrasonic sector scanning plane through mounting, and the location has been memorized by the computer. Controlled by the medical workers, the computer gives instructions to digit-controller, driving the therapeutic head to carry out scanning movement, at the same time, it gives instructions to the power source to turn on or off and regulate the degree of power. The distance between the location of the focal region and the therapeutic head is a fixed focal distance, so the movement of the therapeutic head will drive the focal region formed by the head to carry out parallel movement; therefore, the scanning movement of the head outside the body guarantees the scanning movement of the focal region within the body.

What is claimed is:

1. A high intensity focused ultrasound system, comprising:
    a controllable power supply;
    a B-mode ultrasound scanner;
    a therapeutic bed having a through hole;
    a liquid bag placed in the through hole and having opposite upper and lower portions, the lower portion of the liquid bag being attached to a combined probe, whereby a body portion of a patient lying immediately above the through hole may be scanned and treated by said system; and
    the combined probe comprising:
        a therapeutic head coupled to said controllable power supply for generating and focusing a ultrasound beam on a focal region at a temperature greater than 70 degrees centigrade, said therapeutic head comprising a ultrasound lens and piezoelectric ceramics coupled to said controllable power supply and disposed beneath the ultrasound lens, and
        an imaging probe coupled to said B-mode ultrasound scanner and mounted on a central axis of said therapeutic head so that the focal region of said therapeutic head is fixed at a predetermined location on a scanning plane;
        wherein said liquid bag contains vacuum degassed water having an acoustic impedance similar to that of human tissue, the upper portion of said liquid bag including an opening exposing said vacuum degassed water, said opening being open to an upper surface of said therapeutic bed so as said vacuum degassed water is adapted to be placed in direct contact with the skin of the patient's body portion;
        said system further comprising a multi-dimensional motional apparatus, on which the combined probe is mounted and which is moveable along three-dimensional rectangular coordinate axes and rotatable about one or two rotational coordinate axes, for driving said combined probe, said multidimensional motional apparatus includes a plurality of one-dimensional motional devices each being configured to either translate or rotate said combined probe in a specific direction.

2. The system of claim 1, wherein each of said one-dimensional motional devices comprises a stepping electric motor for moving said combined probe in said specific direction, a position sensor for sensing an actual position of said combined probe, and a closed loop control for coordinating the sensed actual position with the movement by said stepping electric motor.

3. The system of claim 1, wherein said controllable power supply comprises:
    a signal source for generating sine wave signals having a frequency of from 0.2 to about 3.5 MHz;
    a signal modulator for modulating the sine wave signals to continuous waves or low frequency carrier signals having a frequency of from about 10 to about 1000 Hz; and
    a magnifier for duplicating, magnifying and supplying the modulated signals to said therapeutic head.

4. The system of claim 1, wherein a sound intensity of the ultrasound beam is from about 100 W/cm$^2$ to about 10000 W/cm$^2$ in the focal region.

5. The system of claim 4, wherein
    a focal length from the focal region to the therapeutic head is from about 40 to about 280 mm; and
    said focal region has an ellipsoid shape having a short dimension in a longitudinal section in a range of from about 1.1 to about 5 mm, and a long dimension in the longitudinal section in a range of from about 3.5 to about 12 mm.

6. The system of claim 1, wherein said combined probe further comprises a shielded shell and a core disposed inside the shielded shell, said ultrasound lens and said therapeutic head are disposed in the shielded shell and around the core, said imaging probe is disposed within and positioned by the core.

7. A high intensity focused ultrasound system for scanning and treating tumor, said system comprising a combined therapeutic head, a high frequency electric power source, a B-mode ultrasound scanner, a multi-dimensional digit-controlled motional apparatus, a vacuum, degasification water apparatus, a therapeutic bed, and, a computer operation system; wherein
    the combined therapeutic head comprises a therapeutic head which generates therapeutic ultrasound on a focal region at a temperature greater than 70 degrees centigrade and an image-displaying probe of the B-mode ultrasound scanner, the combined therapeutic head is mounted on the multi-dimensional digit-controlled motional apparatus an upper end of the combined therapeutic head is connected to a central hole of the therapeutic bed, through a water bag;
    the water bag is mounted to the central hole of the therapeutic bed a lower end of the water bag is connected to the upper end of the combined therapeutic head;
    the combined therapeutic head is also connected to the high frequency electric power source;
    the image-displaying probe of the B-mode ultrasound scanner is mounted on a central axis of the combined therapeutic head;
    the multi-dimensional digit-controlled motional apparatus is connected to a digit-controlled scanning system;
    the water bag is connected to the vacuum degasification water apparatus;
    the computer operation system is connected separately to the high frequency electric power, B-mode ultrasound scanner, digit-controlled scanning system and vacuum degasification water apparatus;
    wherein said multi-dimensional digit-controlled motional-apparatus consists of a three-dimensional rectangular coordinate and one or two-dimensional rotational coordinate;
    wherein said water bag is an open water bag containing vacuum degasification water having an acoustic impedance similar to that of human tissue and small acoustic attenuation, a ultrasonic wave-emitting surface of the combined therapeutic head is located under the body parts to be treated, the water in the water bag is adapted to contact directly the human skin during treatment.

8. A high intensity focused ultrasound system for scanning and treating tumor in accordance to claim 7, wherein the image-displaying probe of the B-mode ultrasound scanner of the combined therapeutic head is mounted on the central axis of the combined therapeutic head and adjusted so that the focal region of a space point produced, by the therapeutic head falls within an image-displaying plane of the image-displaying probe of the B-mode ultrasound scanner.

9. A high intensity focused ultrasound system for scanning and treating tumor in accordance with claim 7, wherein the multi-dimensional digit-controlled motional apparatus comprises a stepping electric motor that drives a tract base through a ball-screw to move on a ball-tract, a signal of the real position of the motion is taken by a position sensor, then closed-loop control of the multi-dimensional digit-controlled motional apparatus is carried out, the multi-dimensional digit-controlled motional apparatus is formed by repeat addition and combination of a certain number of single-dimensional motional apparatuses.

10. A high intensity focused ultrasound system for scanning and treating tumor in accordance with claim 7, wherein the high frequency electric power source comprises a signal source, a signal modulator, a magnifier, a matching apparatus, a three-phase electric supply, a manual controller, a computer interface, and a displaying apparatus;

the signal modulator is connected separately to the three-phase electric supply, signal source, computer interface and magnifier;

the signal source is connected separately to the three-phase electric supply, magnifier, displaying apparatus, and manual controller;

the magnifier is connected separately to the three-phase electric source and matching apparatus;

the matching apparatus gives out 0.2~3.5 MHz high frequency continuous or pulsed electric supply;

the signal source gives out low pressure high frequency sine wave signal, which is modulated by a signal modulation electric current into a continuous wave or carrier signal of 10 to 1000 Hz.

11. A high intensity focused ultrasound system for scanning and treating tumor in accordance with claim 7, wherein the vacuum degasification water apparatus is a vacuum degasification circulating water apparatus that comprises a vacuum pump, a water circulating pump, a water box, a water temperature regulator, and a controlling electric circuit;

the water box is connected separately to the vacuum pump, water temperature regulator, water circulating pump, combined therapeutic head and water bag;

electric circuit is connected separately to the water circulating pump, water temperature regulator, and vacuum pump;

the combined therapeutic head and water bag are connected separately to the water circulating pump, the vacuum degasification water apparatus treats water, by vacuum degasification, then the treated water is used as ultrasonic coupling medium.

12. A high intensity focused ultrasound system for scanning and treating tumor in accordance with claim 7, wherein the sound intensity of the focal region formed by the combined therapeutic head is 100~10000 W/cm2; the technical parameters of the combined therapeutic head are as follows:

focal distance: 40~280 mm;

working frequency of therapeutic ultrasound: 0.2~3.5 MHz;

shape of focal region: ellipsoid with a short diameter of 1.1~5 mm and a long diameter of 3.5~12 mm;

highest sound intensity at the center of the focal region: over 1000 W/cm2; and focusing angle: 30~120 degrees.

13. A high intensity focused ultrasound system for scanning and treating tumor in accordance with claim 12, wherein regardless of the acoustic attenuation, $I_a=(D/d)^2 ID$, the ratio between average acoustic intensity of the focal region and that of the surface of the combined therapeutic head should be as large as possible.

14. A high intensity focused ultrasound system for scanning and treating tumor in accordance with claim 7, wherein a four-coordinate digit-controlled scanning and one-coordinate rotational apparatus is used as the multi-dimensional digit-controlled motional apparatus;

the power source, B-mode ultrasound scanner, and digit-controlled scanning apparatus all work discontinuously under control of the computer operation system.

15. A high intensity focused ultrasound system for scanning and treating tumor in accordance to claim 7, wherein the whole combined therapeutic head is mounted within a shielded shell;

a water bag base of the water bag is assembled at the front end of the shielded shell; an ultrasonic lens is placed on a core of the image-displaying probe, within the core of the image-displaying probe is the image-displaying probe of the B-mode ultrasound scanner, piezoelectric ceramics are assembled at the back end of the therapeutic head;

an electric supply driving the piezoelectric ceramics to produce ultrasonic wave is provided by a cable.

16. A high intensity focused ultrasound system for scanning and treating tumor, said system comprising: a combined therapeutic head, a high frequency electric power source, a B-mode ultrasound scanner, a multi-dimensional digit-controlled motional apparatus, a vacuum degasification water apparatus, a therapeutic bed, and, a computer operation system; wherein the combined therapeutic head comprises a therapeutic head which generates therapeutic ultrasound on a focal region at a temperature greater than 70 degrees centigrade and an image-displaying probe of the B-mode ultrasound scanner, the combined therapeutic head is mounted on the multi-dimensional digit-controlled motional apparatus, an upper end of the combined therapeutic head is connected to a central hole of the therapeutic bed through a water bag;

the water bag is mounted to the central hole of the therapeutic bed, a lower end of the water bag is connected to the upper end of the combined therapeutic head;

the combined therapeutic head is also connected to the high frequency electric power source;

the image-displaying probe of the B-mode ultrasound scanner is mounted on a central axis of the combined therapeutic head;

the multi-dimensional digit-controlled motional apparatus is connected to a digit-controlled scanning system;

the water bag is connected to the vacuum degasification water apparatus;

the computer operation system is connected separately to the high frequency electric power, B-mode ultrasound scanner, digit-controlled scanning system and vacuum degasification water apparatus;

wherein said water bag is an open water bag containing vacuum degasification water having an acoustic impedance similar to that of human tissue and small acoustic attenuation, a ultrasonic wave-emitting surface of the combined therapeutic head is located under the body parts to be treated, the water in the water bag is adapted to contact directly the human skin during treatment.

17. A high intensity focused ultrasound system for scanning and treating tumor in accordance to claim 16, wherein the image-displaying probe of the B-mode ultrasound scanner of the combined therapeutic head is mounted on the central axis of the combined therapeutic head and adjusted so that the focal region of a space point produced, by the therapeutic head falls within an image-displaying plane of the image-displaying probe of the B-mode ultrasound scanner.

18. A high intensity focused ultrasound system for scanning and treating tumor in accordance with claim 16, wherein the multi-dimensional digit-controlled motional apparatus comprises a stepping electric motor that drives a tract base through a ball-screw to move on a ball-tract, a signal of the real position of the motion is taken by a position sensor, then closed-loop control of multi-dimensional digit-controlled the motional apparatus is carried out, the multi-dimensional digit-controlled motional apparatus is formed by repeat addition and combination of a certain number of single-dimensional motional apparatuses.

19. A high intensity focused ultrasound system for scanning and treating tumor in accordance with claim 16, wherein the high frequency electric power source comprises a signal source, a signal modulator, a magnifier, a matching apparatus, a three-phase electric supply, a manual controller, a computer interface, and a displaying apparatus;

the signal modulator is connected separately to the three-phase electric supply, signal source, computer interface and magnifier;

the signal source is connected separately to the three-phase electric supply, magnifier, displaying apparatus, and manual controller;

the magnifier is connected separately to the three-phase electric source and matching apparatus;

the matching apparatus gives out 0.2~3.5 MHz high frequency continuous or pulsed electric supply;

the signal source gives out low pressure high frequency sine wave signal, which is modulated by a signal modulation electric current into a continuous wave or carrier signal of 10 to 1000 Hz.

20. A high intensity focused ultrasound system for scanning and treating tumor in accordance with claim 16, wherein the vacuum degasification water apparatus is a vacuum degasification circulating water apparatus that comprises a vacuum pump, a water circulating pump, a water box, a water temperature regulator, and a controlling electric circuit;

the water box is connected separately to the vacuum pump, water temperature regulator, water circulating pump, combined therapeutic head and water bag;

the controlling electric circuit is connected separately to the water circulating pump, water temperature regulator, and vacuum pump;

the combined therapeutic head and water bag are connected separately to the water circulating pump, the vacuum degasification water apparatus treats water, by vacuum degasification, then the treated water is used as ultrasonic coupling medium.

21. A high intensity focused ultrasound system for scanning and treating tumor in accordance with claim 16, wherein the sound intensity of the focal region formed by the combined therapeutic head is 100~10000 W/cm2; the technical parameters of the combined therapeutic head are as follows:

focal distance: 40~280 mm;

working frequency of therapeutic ultrasound: 0.2~3.5 MHz;

shape of focal region: ellipsoid with a short diameter of 1.1~5 mm and a long diameter of 3.5~12 mm; highest sound intensity at the center of the focal region: over 1000 W/cm2; and focusing angle: 30~120 degrees.

22. A high intensity focused ultrasound system for scanning and treating tumor in accordance with claim 21, wherein regardless of the acoustic attenuation, $I_a=(D/d)^2$ ID, the ratio between average acoustic intensity of the focal region and that of the surface of the combined therapeutic head should be as large as possible.

23. A high intensity focused ultrasound system for scanning and treating tumor in accordance with claim 16, wherein a four-coordinate digit-controlled scanning and one-coordinate rotational apparatus is used as the multi-dimensional digit-controlled motional apparatus;

the power source, B-mode ultrasound scanner, and digit-controlled scanning apparatus all work discontinuously under control of the computer operation system.

24. A high intensity focused ultrasound system for scanning and treating tumor in accordance to claim 16, wherein the whole combined therapeutic head is mounted within a shielded shell;

a water bag base of the water bag is assembled at the front end of the shielded shell; an ultrasonic lens is placed on a core of the image-displaying probe, within the core of the image-displaying probe is the image-displaying probe of the B-mode ultrasound scanner, piezoelectric ceramics are assembled at the back end of the therapeutic head;

an electric supply driving the piezoelectric ceramics to produce ultrasonic wave is provided by a cable.

* * * * *